United States Patent [19]

Bezwada et al.

[11] Patent Number: 5,653,992
[45] Date of Patent: Aug. 5, 1997

[54] LIQUID ABSORBABLE COPOLYMERS FOR PARENTERAL APPLICATIONS

[75] Inventors: Rao S. Bezwada, Whitehouse Station; Stephen C. Arnold, Franklin, both of N.J.; Shalaby W. Shalaby, Anderson, S.C.; Bernard L. Williams, Martinsville, N.J.

[73] Assignee: Ethicon, Inc., Somerville, N.J.

[21] Appl. No.: 429,375

[22] Filed: Apr. 26, 1995

Related U.S. Application Data

[62] Division of Ser. No. 94,823, Jul. 20, 1993, abandoned.

[51] Int. Cl.⁶ .............................. A61F 2/00; A61K 9/14; A61K 31/785
[52] U.S. Cl. .................. 424/426; 424/486; 424/78.36
[58] Field of Search ................... 424/426, 486, 424/78.36

[56] References Cited

U.S. PATENT DOCUMENTS

| | | | |
|---|---|---|---|
| 3,982,537 | 9/1976 | Bucalo | 128/260 |
| 4,030,499 | 6/1977 | Bucalo | 128/260 |
| 4,054,138 | 10/1977 | Bucalo | 128/260 |
| 4,190,720 | 2/1980 | Shalaby | 528/354 |
| 4,526,938 | 7/1985 | Churchill et al. | 525/415 |
| 4,791,929 | 12/1988 | Jarret et al. | 128/335.5 |
| 4,803,075 | 2/1989 | Wallace et al. | 423/423 |
| 4,818,542 | 4/1989 | DeLuca et al. | 424/491 |
| 4,853,225 | 8/1989 | Wahlib et al. | 424/423 |
| 4,938,763 | 7/1990 | Dunn et al. | 604/891.1 |
| 5,030,457 | 7/1991 | Ng et al. | 424/486 |
| 5,077,049 | 12/1991 | Dunn et al. | 424/426 |
| 5,100,433 | 3/1992 | Bezwada et al. | 606/230 |
| 5,160,737 | 11/1992 | Friedman et al. | 424/401 |
| 5,278,201 | 1/1994 | Dunn et al. | 523/113 |
| 5,278,202 | 1/1994 | Dunnet et al. | 523/113 |
| 5,322,925 | 6/1994 | Muth et al. | 528/354 |
| 5,442,033 | 8/1995 | Bezwada | 528/354 |

FOREIGN PATENT DOCUMENTS

| | | |
|---|---|---|
| 2 390 962 | 12/1978 | France. |
| 42 35 312.2 | 4/1993 | United Kingdom. |
| WO 90/03768 | 4/1990 | WIPO. |
| WO 90/05522 | 5/1990 | WIPO. |
| WO 92/07555 | 5/1992 | WIPO. |

OTHER PUBLICATIONS

Journal of Controlled Release (Elsevier): Biodegradable Block Copolymer Matrices for Long–Acting Contraceptives With Constant Release 22 (1192) 3–14.

Heller et al., "Controlled Drug Release From Bioerodible Hydrophobic Ointments", Biomaterials, May 1990, vol. 11, pp. 235–237.

*Primary Examiner*—Nathan M. Nutter
*Attorney, Agent, or Firm*—Hal Brent Woodrow

[57] ABSTRACT

A sustained release parenteral composition comprising an admixture of at least one drug to be delivered in a therapeutically effective amount and a bioabsorbable lactone polymer containing one or more lactone monomers that is a liquid at body temperature, provided in an amount effective to sustain or extend the release rate of the drug and a method for administering said composition to an animal.

4 Claims, 3 Drawing Sheets

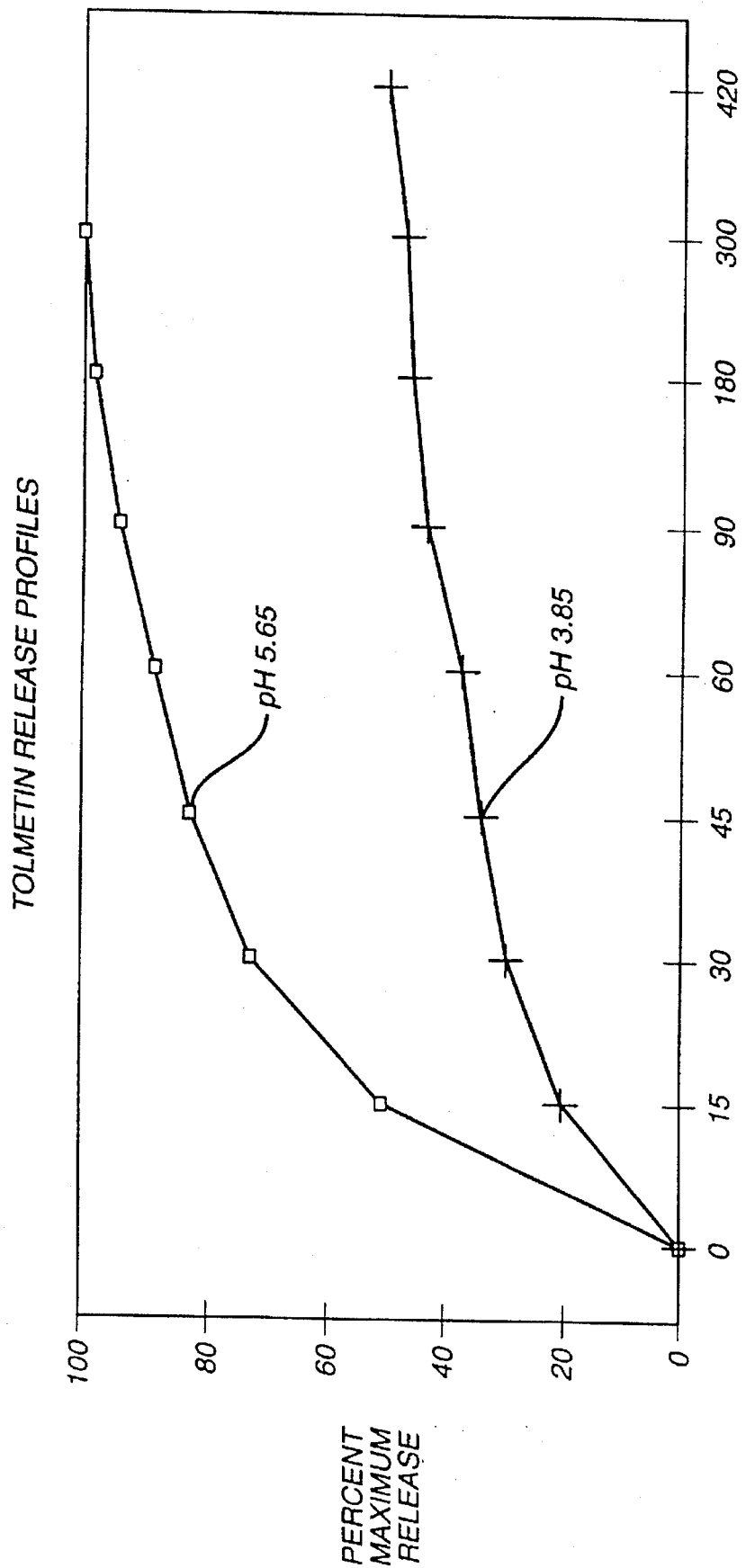

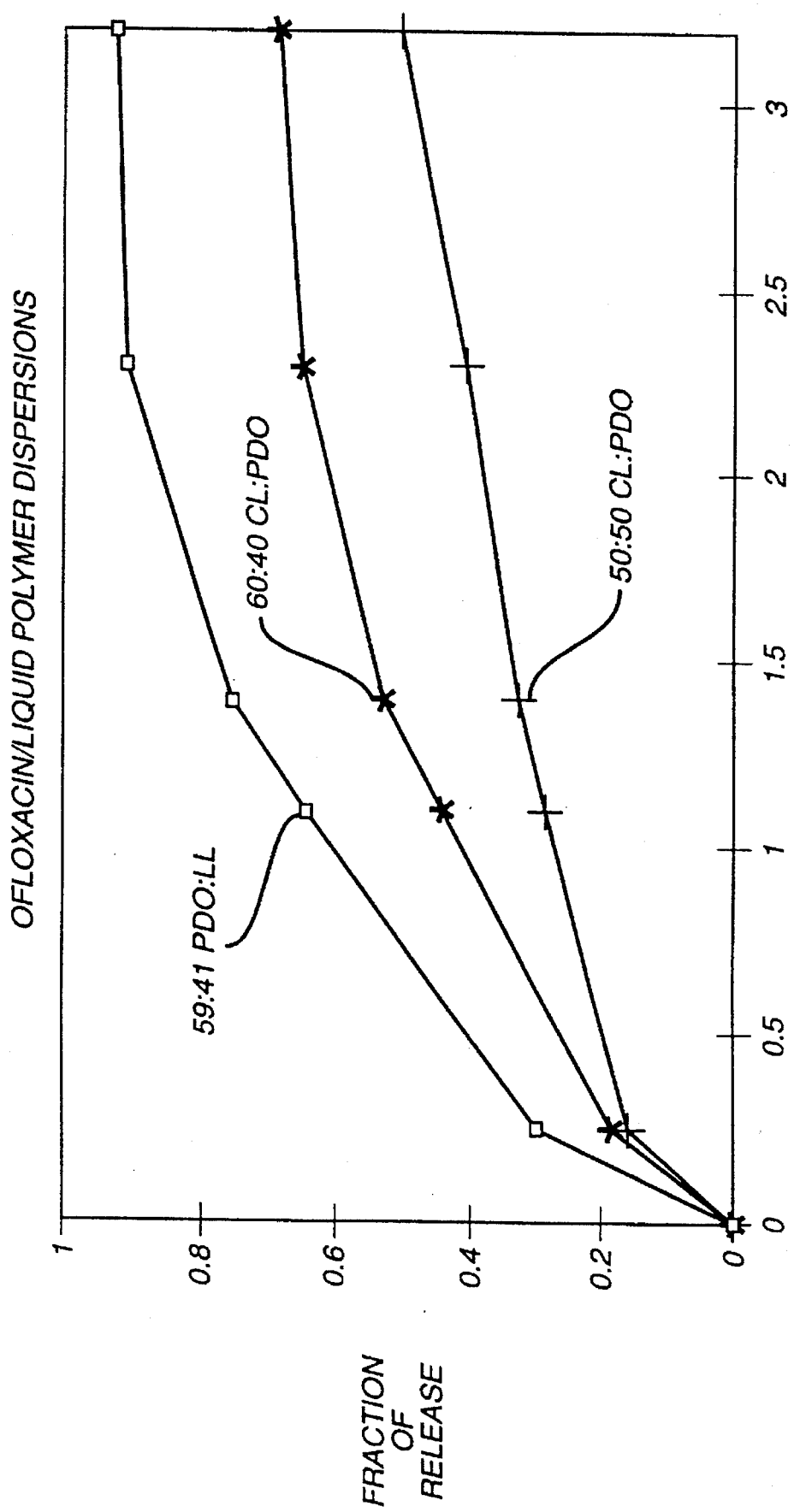

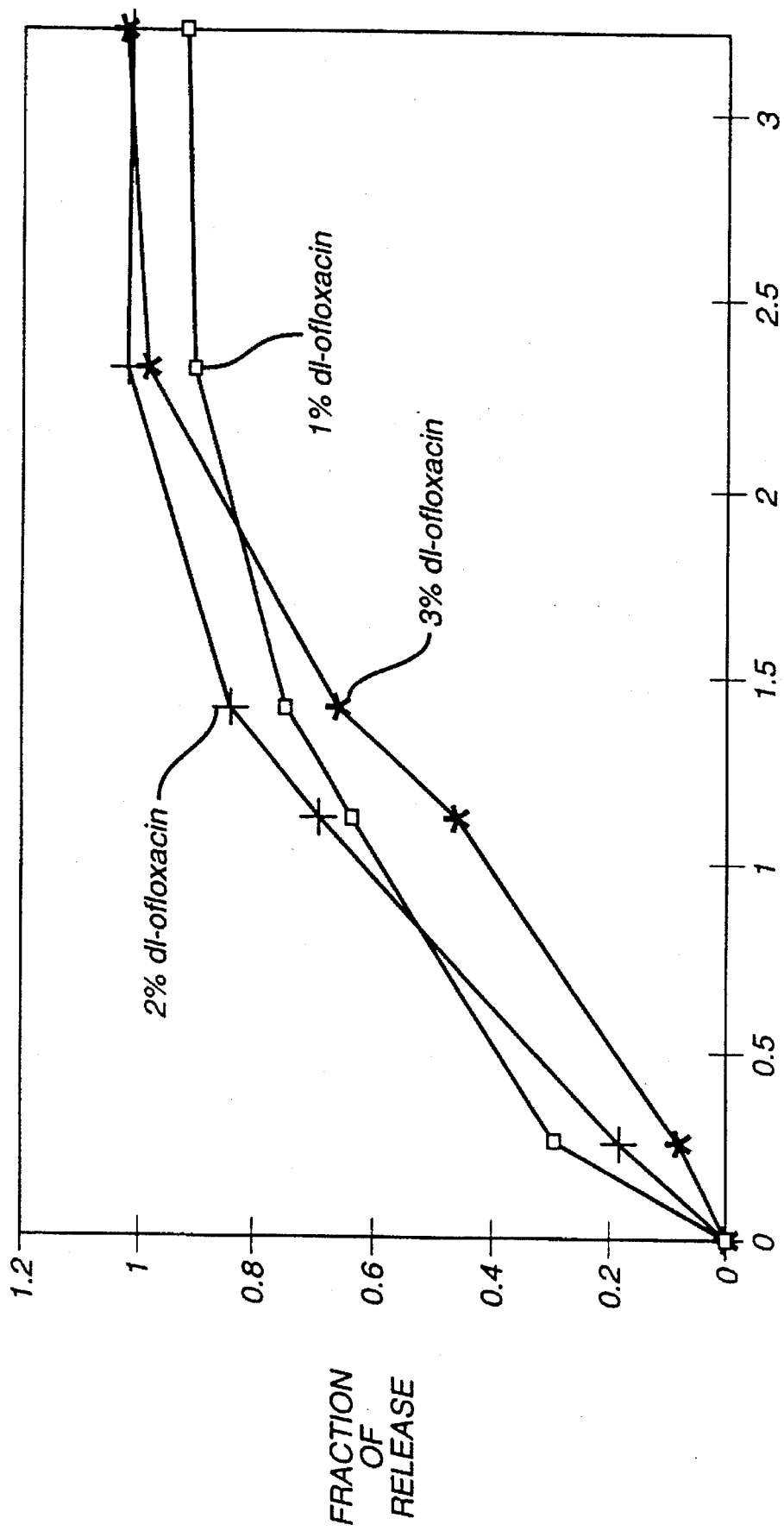

LIQUID ABSORBABLE COPOLYMERS FOR PARENTERAL APPLICATIONS

This is a division of application Ser. No. 08/094,823, filed Jul. 20, 1993 and now abandoned and, which is hereby incorporated by reference.

FIELD OF THE INVENTION

This invention relates to the use of absorbable liquid lactone copolymers for the parenteral administration of drugs. More specifically, it relates to the use of liquid lactone copolymers in parenteral applications for sustained or extended drug delivery.

BACKGROUND OF THE INVENTION

Pharmaceuticals are commonly administered parenterally in isotonic solutions. However, this dosage form is not always well suited for all drugs or prolonged drug therapies. To overcome these and other short comings of this dosage form several new injectable dosage formulations have recently been developed.

The most notable recent development has been the use of bioerodible or bioabsorbable polymers in injectable dosage formulations. Several publications describe these new injectable dosage formulations such as U.S. Pat. No. 3,982,537 and U.S. Pat. No. 4,054,138 issued to Bucalo, U.S. Pat. No. 4,938,763 issued to Dunn et al. and "Biodegradable block copolymer matrices for long-acting contraceptives with constant release" J. Contr. Rel. 32. (1992) 3–14 by Z. W. Gu et al. Each of these publications presents a different formulation that may one day replace conventional parenteral formulations.

Bucalo describes the use of low melting hydrogenated vegetable oils and fats as injectable in-situ implants or injectable microspheres. The implants are formed from vegetable oil or fat that is melted and mixed with a drug. The mixture is then either injected into the patient where the mixture will solidify to form an in-situ implant, or formed into microspheres that are injected. Although this formulation may work for some drugs, the heat necessary to form the liquid mixture of oil or fat and drug will in many cases inactivate or modify the drug being administered.

Dunn et al. describes a different biodegradable in-situ implant that does not require the formulation to be heated. Dunn proposes the use of a liquid polymer carrier that solidifies in-situ by crosslinking or precipitation due to solvent dissipation. Although, Dunn avoids the heat inactivation problems inherent with Bucalo's implants, Dunn's formulations also have significant short comings. The polymer system described by Dunn et al. is based on DL-lactide or L-lactide and ε-caprolactone copolymers. The copolymers are used as prepolymers, which will be derivatized and crosslinked in-situ or dissolved in a solvent. Unfortunately, the crosslinking process requires formulation and mixing of the injectable immediately before administration, which is generally not practical. The solvent based implants, although easier to administer, cannot readily be used because the solvents necessary to dissolve the ε-caprolactone based copolymers that Dunn describe are toxic.

Gu and coworkers describes a formulation containing hard microspheres of a triblock copolymer, namely poly(ε-caprolactone-b-D,L-lactide-b-glycolide) for the controlled release of contraceptives. The microspheres that Gu describe are designed to be injected, thereby avoiding the need to surgically implant a solid dosage. Unfortunately, the kinetics of the pharmaceutical release from these microspheres are complicated by the different release mechanisms of the individual blocks of the triblock copolymer. Although the complicated release mechanism is not an insurmountable obstacle to the use of Gu's microspheres, it makes formulation of sustained release injectables quite difficult.

Thus it would be a significant contribution to the art to provide an injectable dosage form that is easy to administer and provides sustained or extended drug release.

SUMMARY OF THE INVENTION

In one aspect, we have discovered a parenteral composition for injection subcutaneously or intramuscularly into animals comprising an admixture of at least one drug to be delivered in a therapeutically effective amount and a bioabsorbable lactone copolymer containing two or more lactone comonomers that is a liquid at body temperature, provided in an amount effective to sustain or extend the release rate of the drug.

In another aspect of the present invention there is provided a method for parenterally administering a drug subcutaneously or intramuscularly into animals comprising injecting a composition comprising an admixture of a therapeutic amount of at least one drug and a bioabsorbable lactone copolymer containing two or more lactone comonomers that is a liquid at body temperature, provided in an amount effective to sustain or extend the release rate of the drug.

These and other objects and advantages of this invention will be apparent from the disclosure and claims provided herein.

BRIEF DESCRIPTION OF THE FIGURES

FIG. 1 graphically illustrates the in vitro release at ambient temperature of tolmetin over time at pH 5.65 and pH 3.85 from a random copolymer of ε-caprolactone and 1,4-dioxanone. The release profile at pH 5.65 is represented by the squares; the release profile at pH 3.85 is represented by the crosses.

FIG. 2 graphically illustrates the in vitro release at 37° C. of ofloxacin over time at pH 7 in the liquid lactone copolymers produced in Examples 1, 2 and 3. The release profiles of ofloxacin from the copolymers produced in Examples 1, 2 and 3 are represented respectively by the open squares, the asterisks and the crosses.

FIG. 3 graphically illustrates the in vitro release at 37° C. of ofloxacin over time at pH 7 in various concentrations from the liquid lactone copolymer prepared in Example 1.

DETAILED DESCRIPTION OF THE INVENTION

The present invention provides a new parenteral dosage formulation for administering to animals subcutaneously or intramuscularly a therapeutic amount of a drug in a sustained or extended release dosage form. This dosage form may be used in a variety of animals including domestic animals such as dogs, cats, cattle, sheep, horses and primates (including humans).

Many nontoxic bioabsorbable homopolymers, copolymers and terpolymers, that are fluids at body temperature, may be used as a sustained or extended release carrier for intramuscular or subcutaneous injectables. In particular, there are many lactone polymers (including polymers which contain two or more monomers) composed of one or more lactone monomers selected from the group consisting of glycolide, L-lactide, D,L-lactide, 1,4-dioxanone, ε-caprolactone, 1,5-dioxepan-2-one and trimethylene carbonate and other commonly used lactone monomers that are fluids at body temperature. These polymers may be linear, branched, or star branched; statistically random copolymers or terpolymers; segmented block copolymers or terpolymers. Examples of suitable terpolymers are terpolymers containing comonomer combinations selected from the group consisting of glycolide, L-lactide, and p-dioxanone; glycolide, ε-caprolactone and p-dioxanone; and L-lactide, ε-caprolactone and p-dioxanone. These polymers should be purified to remove unreacted monomer which may cause an inflammatory reaction in tissue.

Preferred polymers for use as sustained or extended release carriers are lactone polymers selected from the group consisting of poly(lactide-co-ε-caprolactone), poly(lactide-co-p-dioxanone), poly(lactide-co-1,5-dioxepan-2-one), poly(ε-caprolactone-co-p-dioxanone) and poly(1,5-dioxepan-2-one-co-p-dioxanone). The comonomer ratios of these copolymers should be in the range of from about 70:30 mole percent to about 30:70 mole percent and preferably in the range of from 40:60 mole percent to 60:40 mole percent of the first monomer to second monomer. Most preferably these polymers will be random copolymers.

The copolymer carriers of this invention are characterized by being liquids at body temperature (37° C.) and preferably being liquids at room temperature (being liquids at 25° C.) in the absence of solvents or the like. The copolymers of the present invention should have an inherent viscosity as determined in a 0.1 g/dL solution of hexafluoroisopropanol (HFIP) at 25° C. ranging from about 0.05 to about 0.8, dL/g preferably from about 0.05 to about 0.3 dL/g and most preferably from 0.05 to 0.2 gL/g. A copolymer with an inherent viscosity below 0.05 may fail to significantly impart a controlled release profile to a pharmaceutical, and a carrier copolymer with an inherent viscosity above 0.8 dL/g may be too viscous to be easily administered.

The variety of different therapeutic agents which can be used in conjunction with the copolymers of the invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. Suitable pharmaceuticals for parenteral administration are well known as is exemplified by the *Handbook on Injectable Drugs*, 6th edition, by Lawrence A. Trissel, American Society of Hospital Pharmacists, Bethesda, Md., 1990 (hereby incorporated by reference).

Parenteral administration of a composition of the invention can be affected by either subcutaneous or intramuscular injection. Parenteral formulations of the copolymer may be formulated by mixing one or more therapeutic agents with a liquid copolymer. The therapeutic agent, may be present as a liquid, a finely divided solid, or any other appropriate physical form. Typically, but optionally, the compositions include one or more parenteral additives, e.g., nontoxic auxiliary substances such as diluents, carriers, excipients, stabilizers or the like. Other suitable parenteral additives may be formulated with the copolymer and pharmaceutically active agent or compound, however, if water is to be used it should be added immediately before administration.

The amount of therapeutic agent will be dependent upon the particular drug employed and medical condition being treated. Typically, the amount of drug represents about 0.001% to about 70%, more typically about 0.001% to about 50%, most typically about 0.001% to about 20% by weight of the total composition being common.

The quantity and type of copolymers incorporated into the parenteral will vary depending on the release profile desired and the amount of drug employed. For a more viscous composition, generally a higher molecular weight polymer is used. If a less viscous composition is desired, a lower molecular weight polymer can be employed. The product may contain blends of liquid copolymers to provide the desired release profile or consistency to a given formulation.

The copolymers, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and lactone copolymers may be tested in appropriate in vitro and in vivo models to achieve the desired drug release profiles. For example, a drug could be formulated with a liquid copolymer and injected into an animal. The drug release profile could then be monitored by appropriate means such as, by taking blood samples at specific times and assaying the samples for drug concentration. Following this or similar procedures, those skilled in the art will be able to formulate a variety of sustained release parenteral formulations.

The following examples illustrate, but are not intended to limit, the scope of the claimed invention.

EXAMPLE 1

Copolymerization of 1,4-Dioxanone and L-Lactide
59:41 (mol/mol) 1,4-Dioxanone:L-Lactide Initial Composition A flame dried, 500 mL, single neck round bottom flask was charged with 150.0 grams (1.47 mol) of 1,4-dioxanone, 150.0 grams (1.04 mol) of L-lactide, 60.0 grams (0.65 mol) of glycerol, and 0.25 mL (0.75 mmol) of a 0.33M solution of stannous octoate in toluene. The flask was fitted with a flame dried mechanical stirrer. The reactor flask was flushed with dry nitrogen gas, and an inert atmosphere was maintained throughout the reaction. The reaction mixture was heated to 110° C. for 74 hours. The copolymer was a viscous liquid at room temperature and was vacuum dried at 80° C. for three days (0.1 mm Hg) to remove any unreacted monomers. The copolymer had an inherent viscosity of 0.16 dL/g in hexafluoroisopropanol (HFIP) at 25° C. (c=0.10 g/dL). The copolymer was then extracted with ether for 35 hours using a liquid-liquid extractor. The ether layer was decanted off and the liquid absorbable copolymer was vacuum dried at 60° C. for seven days. The copolymer composition was measured by 300 MHz $^1$H NMR spectroscopy and found to be 36.9 mole percent poly[L-lactide] repeating units, 49.5 mole percent poly[1,4-dioxanone] repeating units, 1.7 mole percent residual 1,4-dioxanone, and 11.9 mole percent unreacted glycerol. This copolymer will be abbreviated as 59:41 PDO:LL.

EXAMPLE 2

Copolymerization of ε-Caprolactone and 1,4-Dioxanone 60:40 (mol/mol) ε-Caprolactone:1,4-Dioxanone Initial Composition A flame dried, 250 mL, single neck round bottom flask was charged with 68.5 grams (600 mmol) of vacuum distilled ε-caprolactone, 40.8 grams (400 mmol) of 1,4-dioxanone, 3.7 milliliters (49 mmol) of propylene glycol (USP grade), and 0.12 milliliters (40 µmol) of a 0.33M stannous octoate solution in toluene. The flask was fitted with a flame dried mechanical stirrer. The reactor flask was flushed with dry nitrogen gas, and an inert atmosphere was maintained throughout the reaction. The reaction mixture was heated to 160° C. for 24 hours, and then, the reaction temperature was reduced to 110° C. and held there for about 24 hours. The copolymer was a viscous liquid at room temperature and was vacuum dried at 80° C. for about 80 hours (0.1 mm Hg) to remove any unreacted monomers. The copolymer had an inherent viscosity of 0.19 dL/g in hexafluoroisopropanol at 25° C. (c=0.10 g/dL). The liquid copolymer exhibited a Brookfield viscosity of 7,620 cps at 25° C. The weight average molecular weight ($M_w$) was 3230 daltons and the number average molecular weight ($M_n$) was 1990 daltons as determined by gel permeation chromatography (GPC) using poly[methyl methacrylate] standards. The copolymer composition was measured by 300 MHz $^1$H NMR spectroscopy and found to be 64.6 mole percent poly[ε-caprolactone] repeating units, 32.6 mole percent poly[1,4-dioxanone] repeating units, and 2.8 mole percent residual 1,4-dioxanone. This copolymer will be abbreviated as 60:40 CL:PDO.

EXAMPLE 3

Copolymerization of ε-Caprolactone and 1,4-Dioxanone 50:50 (mol/mol) ε-Caprolactone:1,4-Dioxanone Initial Composition The procedure of Example 2 was essentially repeated except that the reaction flask was charged with 57.0 grams (500 mmol) of vacuum distilled ε-caprolactone, 51.0 grams (500 mmol) of 1,4-dioxanone, 3.7 milliliters (49 mmol) of propylene glycol (USP grade), and 0.12 milliliters (40 µmol) of a 0.33M stannous octoate solution in toluene. In addition, the copolymerization was conducted at 140° C. for 24 hours. The copolymer was a viscous liquid at room temperature and had an inherent viscosity of 0.22 dL/g in HFIP at 25° C. (c=0.10 g/dL). The copolymer had a Brookfield viscosity of 11,200 cps at 25° C. The $M_w$ was 3290 daltons and the $M_n$ was 1850 daltons as determined by GPC. This copolymer will be abbreviated as 50:50 CL:PDO.

EXAMPLE 4

Copolymerization of ε-Caprolactone and 1,4-Dioxanone 40:60 (mol/mol) ε-Caprolactone:1,4-Dioxanone Initial Composition The procedure of Example 2 was essentially repeated except that the reaction flask was charged with 45.7 grams (400 mmol) of vacuum distilled ε-caprolactone, 61.3 grams (600 mmol) of 1,4-dioxanone, 3.7 milliliters (49 mmol) of propylene glycol (USP grade), and 0.12 milliliters (40 µmol) of a 0.33M stannous octoate solution in toluene. The copolymer was a viscous liquid at room temperature and had an inherent viscosity of 0.18 dL/g in HFIP at 25° C. (c=0.10 g/dL). This copolymer had a Brookfield viscosity of 11,700 cps at 25° C. The $M_w$ was 2960 daltons and the $M_n$ was 1720 daltons as determined by GPC. The copolymer composition was measured by 300 MHz $^1$H NMR spectroscopy and found to be 48.8 mole percent poly[ε-caprolactone] repeating units, 47.8 mole percent poly[1,4-dioxanone] repeating units, and 3.4 mole percent residual 1,4-dioxanone. This copolymer will be abbreviated as 40:60 CL:PDO.

EXAMPLE 5

In Vivo Absorption and Tissue Reaction

The liquid copolymers of ε-caprolactone and 1,4-dioxanone prepared in Examples 2, 3, and 4 were sterilized by filtration and injected into the subcutis and gluteal muscles of rats to observe the absorption and tissue reaction of these liquid copolymers.

Thirty rats were routinely anesthetized, and the skin over the gluteal muscles was prepared for sterile surgery. An incision was made on the dorsal midline over the lumbosacral region, and the gluteal muscles were exposed. For each liquid copolymer, a syringe with a 16 gauge needle was used to inject 60 µL of copolymer into each gluteal muscle, and a syringe with an 18 gauge needle was used to inject 300 µL of copolymer into the subcutaneous tissue on the flank. Each rat received two different copolymers: one in the right gluteal muscle and flank, and another one on the left side. Six rats were humanely killed after 1, 3, 7, 14, and 56 days postoperatively. This procedure allowed evaluation of four subcutaneous and four intramuscular sites for each copolymer each time period. The subcutaneous sites were grossly evaluated for residual copolymer, and histologic sections were evaluated tissue reaction and residual copolymer.

The tissue reaction was minimal to slight at all of the time periods for each copolymer. The implants were still intact after being implanted for 56 days, but they were reduced in size. As expected, the copolymer with the highest proportion of ε-caprolactone (Example 2) was the least absorbed at 56 days.

Absorption was more difficult to measure, but the diameters of all of the subcutaneous implants were about one fourth to one third their original length after 56 days of implantation, implying that the copolymers had been absorbed substantially.

EXAMPLE 6

Liquid Copolymers for Drug Delivery

To demonstrate the use of these liquid copolymers as drug release vehicles, tolmetin was dissolved in a 50:50 (mol/mol) random copolymer of ε-caprolactone and 1,4-dioxanone synthesized as described in Example 2, and the resulting viscous liquid was suspended in two acetate buffers of different pH. The concentration of tolmetin that was released into the buffer over time was monitored by ultraviolet spectroscopy. The results of these experiments are shown in FIG. 1 as a plot of the percent of the maximum release of tolmetin versus time in vitro. As expected, the release of tolmetin was slower in the more acidic medium, because the rate of the neutralization reaction between the carboxyl group of tolmetin and the acetate anion in the buffer decreases with decreasing pH. These data show that liquid absorbable copolymers can be used as drug delivery reservoirs. The exact release profile will depend on the chemical properties of the drug (e.g., solubility, partition coefficients, chemical reaction rates, etc.) and on the experimental conditions (buffer type, pH, and ionic strength in the in vitro experiments and the types of biochemical and cellular reactions in the in vivo experiments that vary from tissue to tissue).

EXAMPLE 7

In Vitro Release Kinetics of d,l-Ofloxacin from Liquid Absorbable Copolymers Suspensions of d,l-ofloxacin in liquid absorbable copolymers were prepared by blending 30 milligrams of d,l-ofloxacin powder into 3.00 grams of liquid copolymer by stirring the mixture with a spatula at ambient temperature until the mixture appeared to be homogeneous, producing suspensions containing 1% d,l-ofloxacin by weight. Approximately 200 milligrams of these suspensions were transferred into open-top cylindrical aluminum cups having diameters of 12 millimeters and heights of 5 millimeters. The cups containing the suspensions of copolymer and drug were carefully submerged in a glass vial containing 25 mL of phosphate buffered saline (PBS), pH 7.0. The aluminum cups constrained all of the test samples into a disk geometry having a diameter of 12 millimeters and an initial thickness of 2 millimeters with one face of the disk in contact with the PBS. The glass vials were sealed with rubber closures and then transferred to a water bath set at 37° C. The samples were continuously agitated by a gentle sinusoidal reciprocating motion having an amplitude of 3.5 cm and a frequency of approximately 1 $\sec^{-1}$. At predetermined intervals, 200 μL of PBS was removed and analyzed by high pressure liquid chromatography for d,l -ofloxacin content. FIG. 2 shows the in vitro release profile of d,l-ofloxacin over a three day period. The fraction of the initial amount of d,l-ofloxacin measured in the PBS was plotted against time for three different liquid copolymer suspensions. The three different liquid absorbable copolymers used in this study were those prepared in Examples 1, 2, and 3.

As illustrated in FIG. 2, the release profile of d,l-ofloxacin depended significantly on the composition of the liquid copolymer in which it was suspended. In general, this dependence of the drug release profile on the composition of the liquid copolymer can be exploited in the field of injectable drug delivery systems. These drug suspensions or solutions in liquid absorbable copolymers can be injected directly into the tissue of interest, and the rate at which the drug is released can be controlled by the proper choice of the liquid copolymer.

EXAMPLE 8

Loading Effects on the Release Profile of d,l-Ofloxacin

Suspensions of d,l-ofloxacin in a 50:50 (mol/mol) random copolymer of 1,4-dioxanone and L-lactide (see Example 1) were prepared by blending 30, 60, and 150 milligrams of d,l-ofloxacin powder into 3.00 grams of liquid copolymer by stirring the mixture with a spatula until the mixture was homogeneous, producing suspensions that contained 1, 2, and 5 percent d,l-ofloxacin by weight. The amount of d,l-ofloxacin released into PBS at 37° C. was determined using the method described in Example 7. FIG. 3 shows the release profile of d,l-ofloxacin for the three different drug loadings. Clearly, the release profile, reported as the fraction of the total amount of d,l -ofloxacin that was detected in the PBS after a given time, was not dependent on the drug loading within the narrow range of one to five weight percent. However, the release profile of d,l-ofloxacin may show a strong dependence on drug loading when another type of liquid copolymer is employed. In general, the dependence of the drug release profile on loading and dose can be measured experimentally by one skilled in the art.

We claim:

1. A parenteral composition for injection subcutaneously or intramuscularly into animals of at least one drug consisting essentially of an admixture of at least one drug to be delivered in a therapeutically effective amount; and a bioabsorbable lactone terpolymer having three or more lactone monomers that is a liquid at body temperature, provided in an amount effective to sustain or extend the release rate of the drug, wherein the inherent viscosity of the terpolymer is between about 0.05 dL/g and about 0.8 dL/g as determined in a 0.1 g/dL solution of hexafluoroisopropanol at 25° C. and the lactone terpolymer contains substantially no unreacted monomer.

2. The parenteral composition of claim 1 wherein the terpolymer is composed of three or more lactone monomers selected from the group consisting of glycolide, L-lactide, D,L-lactide, 1,4-dioxanone, ε-caprolactone, 1,5-dioxepan-2-one and trimethylene carbonate.

3. The parenteral composition of claim 2 wherein the terpolymers are liquids at 25° C.

4. The parenteral composition of claim 1 wherein the terpolymer is a three monomer combination selected from the group consisting of glycolide, L-lactide, and 1,4-dioxanone; glycolide, ε-caprolactone and 1,4-dioxanone; and L-lactide, ε-caprolactone and 1,4-dioxanone.

* * * * *